United States Patent
Krauss et al.

(10) Patent No.: US 7,920,735 B2
(45) Date of Patent: Apr. 5, 2011

(54) METHOD AND DEVICE FOR AUTOMATICALLY DIFFERENTIATING BONES OR OTHER CALCIUM-CONTAINING MATERIALS AND CONTRAST AGENT IN SOFT TISSUE

(75) Inventors: Bernhard Krauss, Burgthann (DE); Michael Grasruck, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1038 days.

(21) Appl. No.: 11/730,271

(22) Filed: Mar. 30, 2007

(65) Prior Publication Data
US 2008/0013672 A1    Jan. 17, 2008

(30) Foreign Application Priority Data
Mar. 31, 2006  (DE) .......................... 10 2006 015 451

(51) Int. Cl.
*G06K 9/00*    (2006.01)
(52) U.S. Cl. .................. 382/132; 378/4; 378/5; 378/21; 378/27; 424/9.4; 600/425
(58) Field of Classification Search .......................... None
See application file for complete search history.

(56) References Cited

U.S. PATENT DOCUMENTS

| 6,904,118 B2 * | 6/2005 | Wu et al. ............................ 378/5 |
| 2003/0043961 A1 * | 3/2003 | Horiuchi ........................ 378/21 |
| 2006/0214110 A1 * | 9/2006 | Kojima et al. ................ 250/394 |

OTHER PUBLICATIONS

German Office Action dated Jan. 5, 2007.

* cited by examiner

*Primary Examiner* — Samir A Ahmed
*Assistant Examiner* — John W Lee
(74) *Attorney, Agent, or Firm* — Harness, Dickey & Pierce, P.L.C.

(57) ABSTRACT

In at least one embodiment, two image data records of two computed tomography pictures of the object are provided that have been recorded in the context of a different spectral distribution of the X-radiation. For voxels of at least one interesting slice, there is calculated from the two image data records a ratio r that is yielded from measured or averaged X-ray attenuation values of the respective voxel or its environment in the context of the different spectral distributions of the X-radiation and prescribed X-ray attenuation values of soft tissue in the context of the different spectral distributions of the X-radiation according to a prescribed calculation rule. Upon overshooting of a threshold value for the ratio r the respective voxel is assigned either contrast agent or calcium-containing material as a function of the magnitude of r.

20 Claims, 2 Drawing Sheets

Material assignment

METHOD AND DEVICE FOR AUTOMATICALLY DIFFERENTIATING BONES OR OTHER CALCIUM-CONTAINING MATERIALS AND CONTRAST AGENT IN SOFT TISSUE

PRIORITY STATEMENT

The present application hereby claims priority under 35 U.S.C. §119 on German patent application numbers DE 10 2006 015 451.7 filed Mar. 31, 2006, the entire contents of each of which is hereby incorporated herein by reference.

FIELD

Embodiments of the present invention generally relate to a method and/or a device for automatically differentiating bones or other calcium-containing materials and contrast agent in soft tissue of an object area. For example, it may relate to one where two computed tomography pictures of the object area are recorded in the context of a different spectral distribution of the X-radiation, and there are reconstructed from the raw data of the two computed tomography pictures two image data records of the object area that include X-ray attenuation values of voxels of the object area in the context of the respective spectral distribution of the X-radiation.

BACKGROUND

In many investigations, by way of computed tomography, the patient is administered a contrast agent in order, in particular, to be able to identify blood vessels clearly in the CT images obtained. However, when viewing the CT images other body constituents than bone can have a disturbing effect, since they likewise strongly absorb the X-radiation. Such areas are therefore removed from the images during image reprocessing, if appropriate by computer devices. Again, the identification of other calcium-containing areas, or ones enriched with calcium, such as plaques in vessels or calcium-containing kidney stones requires a distinction to be made between contrast agent and these calcium-containing areas or materials, in order to be able to highlight these, for example when displaying them in a CT image. However, a semiautomatic or automatic segmentation of bones or other calcium-containing areas requires contrast agent and the calcium-containing material in the respective image data to be distinguished as automatically as possible.

Various approaches have been adopted to date in order to distinguish these materials. Thus, a CT scan can be carried out in each case before and after the administration of the contrast agent. The raising of the X-ray attenuation value by the contrast agent is measured by image registration and subtraction of the two CT images. Bones or other calcium-containing areas appear in this case as unchanged regions with a high X-ray attenuation value. A further possibility resides in carrying out a classification in the CT image of a single CT scan on the basis of the level of the X-ray attenuation values. However, this frequently requires additional evaluation of local statistical variables or morphological features in order to obtain results that are to some extent reliable.

SUMMARY

At least one embodiment of the present invention specifies a method and/or a device for automatically differentiating bones or other calcium-containing materials and contrast agent in soft tissue of an object area by way of computed tomography that supplies reliable results in a simple way.

In at least one embodiment of the present method, two computed tomography pictures of the object area are recorded in the context of a different spectral distribution of the X-radiation or different X-ray energy, and there are reconstructed from the raw data of the two computed tomography pictures two image data records of the object area that include X-ray attenuation values of voxels of the object area in the context of the respective spectral distribution of the X-radiation. X-ray attenuation values can be understood here both as the attenuation coefficients $\mu$ and as values derived therefrom, such as the CT value.

Two computed tomography pictures are recorded by using a multi-energy computer tomograph, preferably a so-called dual energy computer tomograph, with the aid of which it is possible simultaneously, or at least almost simultaneously, to record two computed tomography pictures with a different spectral distribution of the X-radiation or different X-ray energy. Different techniques for generating two computed tomography pictures with a different spectral distribution of the X-radiation are fundamentally known to the specialist. It is possible for this end, for example, to make use of a number of X-ray sources with a different tube voltage, different detectors of different spectral sensitivity, different filters in front of the X-ray sources and/or X-ray detectors, or else of a combination of said techniques.

In at least one embodiment of the present method, there is calculated from the two image data records for each voxel of at least one interesting slice of the object area a ratio r that is yielded in the following way:

$$r = \frac{x_1 - o_1}{x_2 - o_2}.$$

In this equation, $x_1$ represents either the measured X-ray attenuation value of the voxel in the context of one of the two different X-ray energies, or an X-ray attenuation value averaged for this X-ray energy, which will be examined more closely later. In the same way, $x_2$ represents either the measured X-ray attenuation value of the voxel in the context of the other X-ray energy, or an appropriately averaged X-ray attenuation value. The two X-ray attenuation values $x_1$, $x_2$ can either be extracted directly from the two image data records, or be calculated therefrom. The values $o_1$ and $o_2$ that also occur represent the X-ray attenuation values of soft tissue in the context of the two X-ray energies. These values are prescribed. They are either already known, or can be determined in advance. The X-ray attenuation values of blood are virtually identical, and so no distinction is made from what follows between blood and soft tissue.

The value, determined in this way for the relevant voxel of the ratio r, or a value r' derived therefrom, is compared with a threshold value of r. A voxel whose value of r or r' lies above the threshold value is assigned either the contrast agent or calcium-containing material as a function of the magnitude of r or r'. High values of r or r' that lie above a threshold $r_{co,min}$ characterized regions with contrast agent. This further prescribed threshold $r_{co,min}$ therefore enables the differentiation of contrast agent and calcium-containing material in the soft tissue investigated.

After at least the interesting slice has been completely processed, contrast agent and bone (or other calcium-containing areas) can be differently marked in color in the display of a CT image of the object area, and so the viewer can immediately distinguish straight away between the two material groups. Furthermore, on the basis of the assignment of said materials to the voxels it is possible to apply to the image data records automatic segmentation algorithms with the aid of which, for example, bones can be removed computationally from the images.

At least one embodiment of the present method and/or the associated device therefore enable the automatic differentiation of bones or other calcium-containing materials and contrast agent in computed tomography pictures. A higher reliability of differentiation is achieved by the proposed method steps than can be achieved with the aid of a simple formation of threshold value with the aid of a single CT scan.

The basis of at least one embodiment of the present method is a 3-material decomposition. In this 3-material decomposition, the respective voxel is interpreted as a mixture of the base materials of soft tissue and/or blood, bone and/or calcium-containing material and contrast agent. It has been recognized here that contrast agent can then be reliably distinguished from calcium-containing material from the ratio r or r'. The variable r or r' resulting from the 3-material decomposition leads to a very good distinguishing of material without having the process to assume typical patients or typical body regions. The possibility of recording two computed tomography pictures simultaneously, or at least virtually simultaneously, also eliminates the complication of the registration that is required before and after the administration of contrast agent in the case of two separate CT scans. The present method also eliminates making a distinction by evaluating local statistical variables or morphological features, as is generally required in the case of simple CT scans in order to raise the reliability.

In an advantageous development of at least one embodiment of the method, a three-dimensional volume area with a prescribed extent around the voxel is firstly defined for each voxel. The three-dimensional volume area preferably constitutes a spherical volume, but can also exhibit another shape, for example a cuboid. All the voxels in the case of which a mean value or a weighted mean value of the two X-ray attenuation values from the two image data records lie above a prescribed threshold value for contrast agent and calcium-containing materials are then selected inside the volume area.

Alternatively, there are selected from this volume area a prescribed number of voxels that have the highest mean values or weighted mean values of the X-ray attenuation values inside the volume area. An averaged X-ray attenuation value of the selected voxels is then calculated separately for each image data record, in order to determine the ratio r from the two averaged X-ray attenuation values. The voxel respectively concerned and around which the volume area is formed is also denoted as central voxel below. This step enables a selection of neighboring voxels of the central voxel that display contrast agent or bone or calcium-containing areas with high probability without causing smearing of a constant range. The use of the weighted mean value described below has the advantage that no preference comes to be given to a material as a function of the image noise ratio q.

The mean value of the X-ray attenuation values of a voxel correspond in this case to the arithmetic mean value of the two X-ray attenuation values. The weighted mean value constitutes, by contrast, a combined X-ray attenuation value from voxels that also depends on the image noise ratio q between the images of the two computed tomography pictures.

This weighted mean value $x_m$ is calculated using the following rule:

$$x_m = \frac{x_1 - m \cdot x_2}{1 - m}, \text{ in which case } m = -\frac{q^2}{r_{co,min}}.$$

$x_1$ and $x_2$ represent the X-ray attenuation values, or HU values (HU: Hounsfield Units), for the two different X-ray energies. q represents the ratio of the image noise of the images of the two computed tomography pictures. The image noise ratio is yielded from $q=ds_1/dx_2$, which $dx_1$ and $dx_2$ represent the statistical errors, that is to say the standard deviation, of the X-ray attenuation values $x_1$ and $x_2$. The value $r_{co,min}$ is a prescribed threshold value that specifies the lower threshold of the ratio r for contrast agent. This value is known or can be determined in advance.

The voxels are then selected inside the three-dimensional volume area preferably on the basis of the weighted mean value $x_m$. All the voxels for which this weighted mean value $x_m$ lies above a threshold value that represents a lower limit for the presence of contrast agent and/or calcium-containing material are selected. Alternatively, a fixed number of voxels are selected that have the highest weighted mean values of the X-ray attenuation values inside the volume area. This mode of procedure based on the weighted mean value that represents a value dependent on the image noise ratio q substantially reduces the risk of an erroneous selection, caused by the image noise, and so a more reliable result is attained. The ratio q of the image noise of the two image data records that is required for this purpose can already be known for the computed tomography installation being used, or be determined in advance from the two image data records, or else other image data records, for example topograms recorded in advance.

In a development of at least one embodiment of the method, the voxels that are present in the three-dimensional volume area and whose mean values or weighted mean values lie above the prescribed threshold value for contrast agent and calcium-containing materials are counted. The determination of the ratio r of the averaged attenuation values is then carried out only in the case of central voxels where inside the volume area a prescribed minimum number ($n_{min}$) of voxels have a mean value or a weighted mean value of the two X-ray attenuation values above the prescribed threshold value for contrast agent and calcium-containing materials. If, however, the number determined lies below this minimum number, no further kind of calculation is carried out for the central voxel. It is then assumed that this voxel does not constitute a site with contrast agent or calcium-containing material in the object area investigated.

In the preferred refinement of at least one embodiment of the method, before the calculation of the ratio r a check is carried out as to whether there occurs in a three-dimensional volume area of prescribed extent around the central voxel a higher proportion of voxels with a mean value of the X-ray attenuation values that lies above a prescribed threshold value for contrast agent and calcium-containing materials. To this end, it is preferred to prescribe a (high) minimum number ($n_{LOOK}$) of voxels. A high proportion indicates a site in a bone or other calcium-containing material. If, however, a few voxels lie in the value range of soft tissue or blood, this indicates a site in the transition region between soft tissue and bone or calcium-containing material.

In the case of a high proportion of voxels whose mean value of the X-ray attenuation values lies above the threshold value for contrast agent and calcium-containing materials, the subsequent steps for forming the ratio r are carried out directly for the central voxel. If, however, the prescribed minimum number is not reached, that is to say a few voxels lie in the value range of soft tissue, in general a directly adjacent neighboring voxel is sought that has the highest mean value or highest weighted mean value of the X-ray attenuation values. This step can also be iterated several times, depending on image resolution.

The subsequent steps for calculating the ratio r are then carried out with the aid of the neighboring voxel determined in this way, but the material assignment resulting therefrom is done, however, to the central voxel. The effect of this preferred configuration of at least one embodiment of the method is, firstly, to enable the separation of contrast agent and bone or calcium-containing materials in neighboring areas. Secondly, the transition to neighboring voxels with higher mean values avoids an evaluation in the boundary range between soft tissue and contrast agent or bone and/or calcium-containing material. Here, noise has a stronger effect, and even a slightly different modulation transfer function for the two different X-ray energies would render chemical classification more difficult.

In a very advantageous development of at least one embodiment of the method, the ratio r before the material assignment is corrected with the aid of a correction term $r_{corr}$ dependent on the diameter of the object investigated, in order to obtain the derived value r':

$$r'=r+r_{corr}(d)$$

d corresponding to a mean diameter of the object. It was found here that for existing computer tomographs a linear function $r_{corr}=a_{diam} \cdot (d-20 \text{ cm})$ lead to very good results. This correction term should be used if the measured X-ray attenuation value of the contrast agent is a function of object diameter.

The device for automatically differentiating bones or other calcium-containing materials and contrast agent in soft tissue of an object area includes, in addition to a memory unit for the two image data records as main constituent, a determination module that carries out the calculations and determinations in accordance with at least one embodiment of the previously described method and, if appropriate, the individual developments of at least one embodiment of this method. The determination module is in this case preferably implemented in the image computer of a computed tomography installation that can supply the raw data for the two computed tomography pictures in the context of a different spectral distribution of the X-radiation. In this case, the device also includes an image reconstruction module that reconstructs the two image data records of the object area from the raw data of the two computed tomography pictures.

In one refinement, at least one embodiment of the device can, however, also include only the determination module with the memory unit, and an interface via which the already reconstructed image data records from the two computed tomography pictures are received. The determination module is preferably connected to an image display module via which the CT images can be pictorially displayed with areas containing contrast agent and containing calcium in a fashion differentiated by color.

BRIEF DESCRIPTION OF THE DRAWINGS

The present method is explained once again briefly below with the aid of an example embodiment in conjunction with the drawings, in which.

DETAILED DESCRIPTION OF THE EXAMPLE EMBODIMENTS

Figure 1:
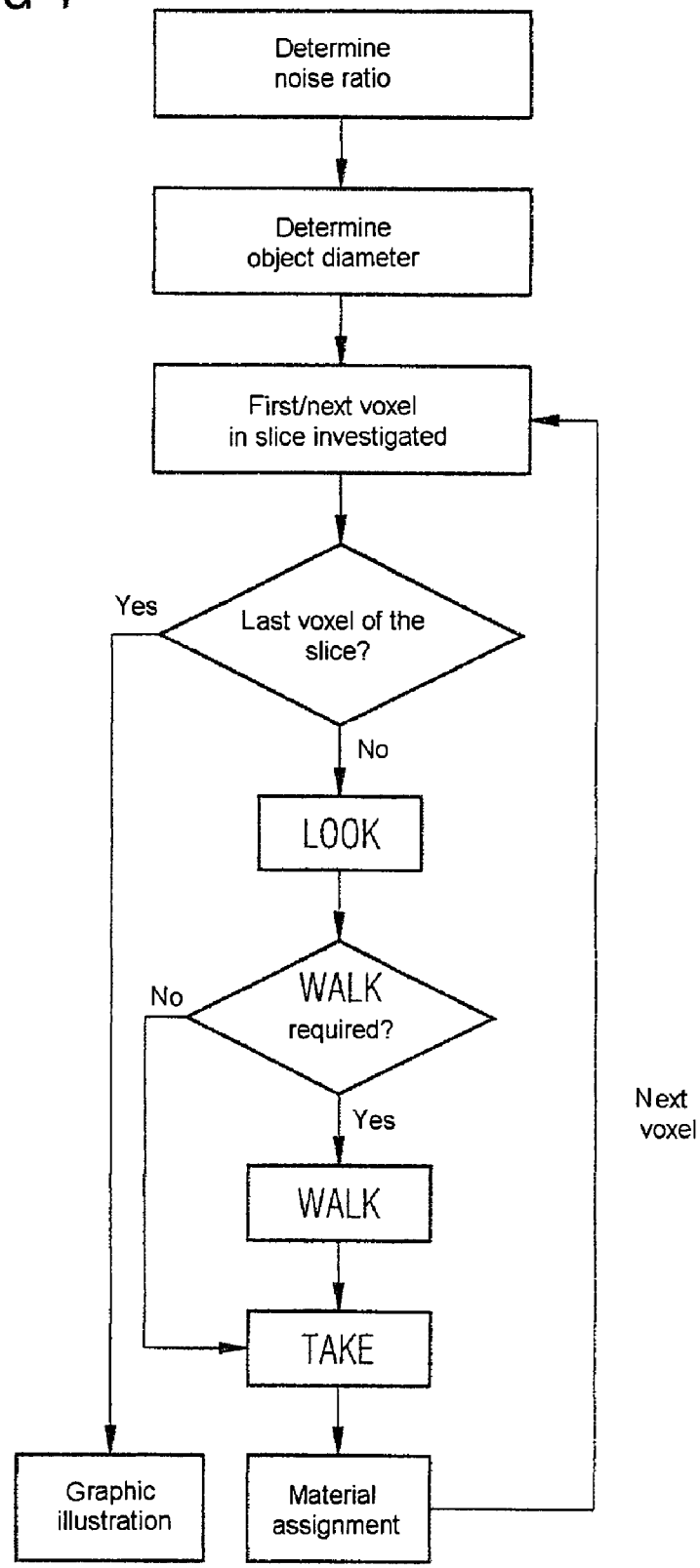
FIG. 1 shows an example of a method cycle in carrying out an embodiment of the present method.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

The terminology used herein is for the purpose of describing particular embodiments only and is not intended to be limiting of the present invention. As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Referencing the drawings, wherein like reference numerals designate identical or corresponding parts throughout the several views, example embodiments of the present patent application are hereafter described.

In the present example embodiment, a dual energy computer tomograph is used to carry out a dual energy CT scan of the object, in which raw data are simultaneously obtained in the context of two different X-ray energies. These different X-ray energies are obtained by means of a different tube voltage of the X-ray tubes used, 80 kV and 140 kV in the present example. Two CT images are reconstructed independently of one another from the raw data via known reconstruction algorithms. Each of the two image data records obtained in this case comprises for each voxel of the investigation volume a corresponding HU value for the respective X-ray energy.

Irrespective of the data recording and the computer tomograph used, it should be ensured in this case that the HU values for the body materials to be differentiated are to some extent stable when they occur or are positioned at different sites inside the object being investigated. This is, however, the case for most commercially available computer tomographs.

The example, described below, of carrying out an embodiment of the present invention splits into a preprocessing and a main part. During preprocessing, a mean object diameter d and the ratio of the image noise between the image for 80 kV and the image for 140 kV are determined if these variables are not already known.

If the measured HU value of the contrast agent depends on the object diameter ab, the mean diameter d of the scanned object must be determined. This is required later for a small, but very useful correction. The mean diameter d can, for example, be calculated by the integral of the HU value x over the area A occupied by the object in the slice image considered:

$$d = \sqrt{\frac{1}{\pi \cdot 1000HU} \int dA(x + 1000HU)}$$

If the ratio of the image noise is not known, this ratio q can, for example, be determined approximately from the object diameter or the measured noise of the HU values of air. It is possible to this end, for example, to calculate for both tube voltages the mean noise for all the pixels of the slice below a certain threshold, for example, below −950 HU, in the upper half of the image, and to form the ratio subsequently. It is likewise possible to determine this ratio from a previously recorded topogram, for example.

In addition to the slice being investigated, a number of voxel slices above and below it are also required for the main portion of the processing. The term "combined HU value" further denotes a weighted mean value $x_m$, dependent on the image noise ratio q, of the HU values at 80 kV and 140 kV ($x_{80}$ and $x_{140}$), respectively. This can be calculated from the ratio q and the threshold value $r_{co,min}$ used later, for contrast agent:

$$x_m = \frac{x_{80} - m \cdot x_{140}}{1 - m}, \text{ in which case } m = -\frac{q^2}{r_{co,min}}.$$

By contrast therewith the term "averaged HU value" is calculated as the arithmetic mean from the HU values for 80 kV and 140 kV, $x_{80}$ and $x_{140}$.

The following four steps, of which the first three are denoted with reference to FIG. 1 as LOOK step, WALK step and TAKE step, are then carried out for each voxel in the slice being investigated.

1. LOOK step: If high averaged HU values that lie substantially higher than the HU values of normal soft tissue (for example, 100 HU) prevail in a three-dimensional spherical environment of the voxel, this environment must be directly evaluated. The following WALK step is then skipped. The basic threshold is prescribed as a number $n_{LOOK}$ for contrast agent/bone voxels above which the WALK step is eliminated.
2. WALK step: If, however, relatively low averaged HU values prevail in the environment, but the averaged HU value of the central voxel lies above that of typical soft tissue, and a steeper gradient exists in the combined HU values, there is a high probability that contrast agent or bone and/or calcium-containing material is located in the vicinity. The neighbor with the highest combined HU value is then selected as new central voxel. It is possible here to prescribe a minimum difference (HU) between the central voxel and the neighboring voxel, below which no transition to the neighboring voxel is performed. This step ($n_{step}$) is repeated until the expected range of the image resolution is reached, or the gradient flattens off strongly.
3. TAKE step: Once again, a spherical environment of the last central voxel is considered. The $n_{av}$ voxels with the highest combined HU values are now selected, the number $n_{av}$ being prescribed. Bone voxels or contrast agent voxels that are as "pure" as possible are selected in this way. A mean HU value $x_{80}$ for 80 kV, and a mean HU value $x_{140}$ for 140 kV are calculated for the selected voxels, this being done in each case by averaging over the HU values of all the selected voxels. If the averaged HU value lies above the contrast agent/bone threshold for less than $n_{min}$ voxels in the volume considered, the following step is eliminated, and no material assignment is made.
4. 3-material decomposition: The selected voxels are interpreted as a mixture of the base materials of soft tissue (HU values: $o_{80}$ and $o_{140}$), bone and/or calcium-containing material and contrast agent. The ratio $$r = \frac{x_{80} - o_{80}}{x_{140} - o_{140}}$$

is calculated. This ratio is optionally corrected by means of a term $r_{corr}$ that depends on object diameter: $r' = r + r_{corr}(d)$. In this way, a value $r_{corr} = a_{diam} \times (d - 20 \text{ cm})$ that ensures a realistic correction is found for existing CT scanners.

High values of r' characterize regions with, for example, iodine-containing contrast agent; medium values of r' are measured for bone; low values of r' are needed for cartilage and plaque. The material determined by the value of r' is now assigned to the original voxel from the first step.

Once the image stack or the three-dimensional image data records have been completely processed, the material map thus prepared can be used to mark bone and/or calcium-containing material and contrast agent with different colors, or to remove bone from the images by computation.

Figure 2:
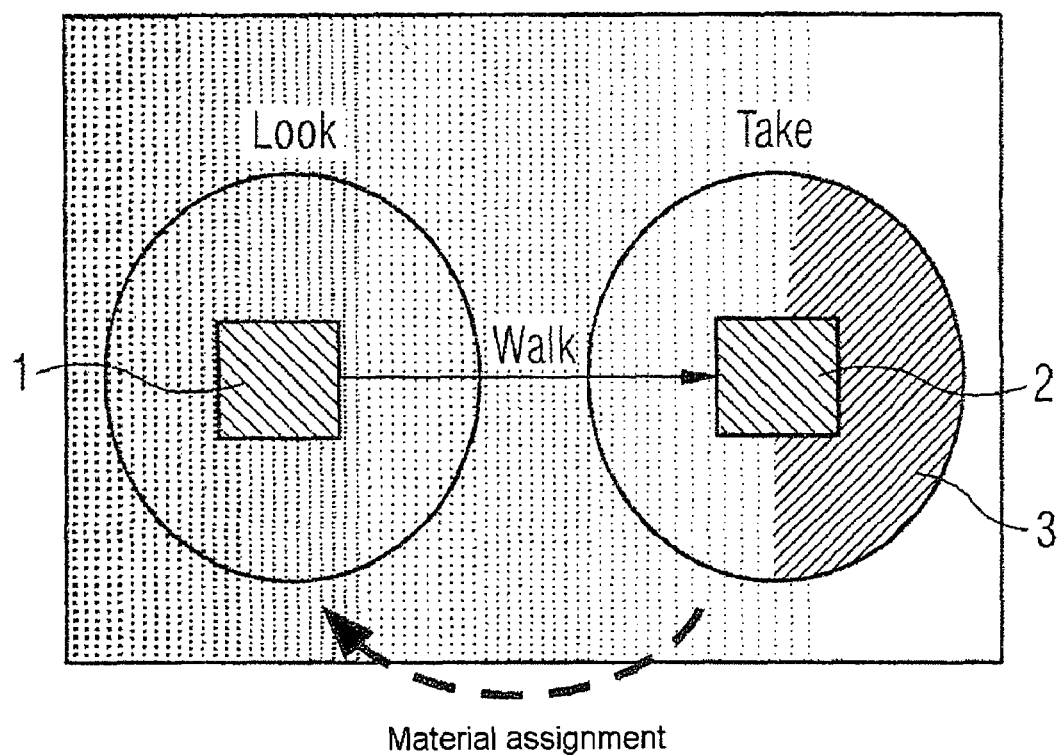
FIG. 2 shows a graphic illustration of a variant of an embodiment of the present method.

The combination of the first three steps (LOOK-WALK-TAKE) that is used in the present example leads in the boundary region between soft tissue and contrast agent or between soft tissue and calcium-containing material and/or bone to a material assignment such as is illustrated graphically in FIG. 2 for the purpose of explanation. It is established in this case in the LOOK step whether the central voxel 1 currently being considered lies in the vicinity of a boundary surface between contrast agent or calcium-containing material and soft tissue. If this is the case, it is not the central voxel itself or its immediate environment that is valued, but the environment of a neighboring voxel 2 which, because of the higher averaged HU value, in each case lies inside the material with a high X-ray attenuation value. A valuation in the boundary region between soft tissue and the corresponding material is thereby avoided.

The following parameters are required in this example to carry out an embodiment of the method:

| Parameter | Meaning |
| --- | --- |
| $x_{min}$ | Lower threshold (HU) for bone/contrast agent voxels |
| $n_{LOOK}$ | LOOK: minimum number of contrast agent/bone voxels such that WALK is eliminated |
| $s_{TAKE}$ | LOOK/TAKE: radius of the volume considered |
| $n_{step}$ | WALK: maximum number of WALK steps |
| $d_{min}$ | WALK: minimum difference (HU) between central voxel and neighboring voxel to be selected |
| $s_{WALK}$ | WALK: radius of the volume considered (normal = 1) |
| $n_{min}$ | TAKE: minimum number of voxels above bone/contrast agent threshold |
| $n_{av}$ | TAKE: number of voxels used with maximum HU value $x_m$ |
| $o_{80}$ | HU value of soft tissue for 80 kV |
| $o_{140}$ | HU value of soft tissue for 140 kV |
| $a_{diam}$ | Linear coefficient for correcting r as a function of d |
| $r_{co,min}$ | Lower threshold of r for contrast agent voxels |

The individual parameters for the number of voxels, and the thresholds can be prescribed as a function of the image quality and the desired illustration. The following example values lead to good results: $n_{LOOK}$=from 78 to 81; $s_{TAKE}$=1

(for calcifications) or 2 (for bones); $n_{step}=2$; $d_{min}=30$; $s_{WALK}=1$ (for calcifications) or 2 (for bones); $n_{min}=50$ (for bones) or 7 (for calcifications); $n_{av}=45$ (for bones) or 3 (for calcifications). The thresholds $x_{min}$ and $r_{co,min}$ are selected as a function of the computed tomography installation and the recording parameters. The linear coefficient $a_{diam}$ is likewise selected as a function of the computed tomography installation.

When applying an embodiment of the present method, it should be distinguished whether bones are being distinguished from contrast agent, or whether other calcium-containing materials are being distinguished from contrast agent. Because of the bone marrow stored, bone is chemically more inhomogeneous than calcium-containing plaque or kidney stones. A very high spatial resolution is specifically required for lime containing plaque. Consequently, the parameters $s_{TAKE}$, $s_{WALK}$ and $n_{step}$ should typically be selected to be smaller in conjunction with the same voxel size in such a case. It is therefore also necessary to reduce $n_{min}$ and $n_{av}$.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automatically differentiating at least one of bones and other calcium-containing materials and contrast agent in soft tissue of an object area, in which the method comprising:
    recording two computed tomography pictures of the object area at different spectral distribution of X-radiation,
    reconstructing from raw data of the two computed tomography pictures two image data records of the object area that include X-ray attenuation values of voxels of the object area at the respective spectral distribution of the X-radiation, each voxel including two X-ray attenuation values corresponding to the two image data records,
    calculating from the two image data records, for voxels of at least one slice of the object area, a ratio r,
    said ratio r resulting from at least one of the two X-ray attenuation values of the respective voxel and two averaged X-ray attenuation values obtained by averaging the X-ray attenuation values of voxels inside a volume around the respective voxel in the respective image data record, and X-ray attenuation values o1, o2 of soft tissue or blood at the respective spectral distribution of the X-radiation, using the following equation, $$r = \frac{x_1 - o_1}{x_2 - o_2}$$

x1, x2 being the X-ray attenuation values or averaged X-ray attenuation values at the respective spectral distribution of the X-radiation; and
    assigning to the respective voxel, upon overshooting of a threshold value for at least one of the ratio r and a value r' derived therefrom, the contrast agent or calcium-containing material as a function of a magnitude of at least one of r and r'.

2. The method as claimed in claim 1, further comprising:
    defining, for each voxel, a three-dimensional volume area around the voxel,
selecting inside the volume area all the voxels, if at least one of a mean value and a weighted mean value of the two X-ray attenuation values of the voxels lie above a threshold value for contrast agent and calcium-containing materials, or
    selecting a number of voxels that have at least one of highest mean values and weighted mean values of the X-ray attenuation values inside the volume area, and
    calculating an averaged X-ray attenuation value of the selected voxels is separately for each image data record to determine the ratio r from the two averaged X-ray attenuation values.

3. The method as claimed in claim 1, further comprising:
    defining, for each voxel, a three-dimensional volume area around the voxel,
    selecting inside the volume area all the voxels, in the case of which at least one of a mean value and a weighted mean value of the two X-ray attenuation values of the voxels lie above a threshold value for contrast agent and calcium-containing materials, or
    selecting a number of voxels that have at least one of highest mean values and weighted mean values of the X-ray attenuation values inside the volume area, and
    calculating an averaged X-ray attenuation value of the selected voxels separately for each image data record to determine the ratio r from the two averaged X-ray attenuation values, the determination of the ratio r of the averaged attenuation values being carried out only for voxels inside the volume area having at least one of a mean value and a weighted mean value of the two X-ray attenuation values above the threshold value for contrast agent and calcium-containing materials that is above a minimum number.

4. The method as claimed in claim 2, wherein the weighted mean value $x_m$ is obtained from the following calculation rule, $$x_m = \frac{x_1 - m \cdot x_2}{1 - m}, \text{ in which case } m = -\frac{q^2}{r_{co,min}},$$

$x_1$ and $x_2$ representing the two X-ray attenuation values of the voxel at the two different spectral distributions of the X-radiation, $r_{co,min}$ representing a lower threshold value of the ratio r for contrast agent, and q representing a ratio of values of image noise of the images of the two image data records.

5. The method as claimed in claim 4, wherein the ratio q of the image noise is determined in a preprocessing step from the two image data records or topograms recorded in advance.

6. The method as claimed in claim 1, further comprising:
    before calculating the ratio r, checking whether a high proportion of voxels with a mean value of the X-ray attenuation values from the two image data records that is above a threshold value for contrast agent and calcium-containing materials occurs in the three-dimensional volume area around the voxel, and
    if a proportion is below a minimum value, searching for a neighboring voxel from a group of neighboring voxels that has at least one of a highest mean value and weighted mean value of the X-ray attenuation values, repeating the checking once or several times, starting from the neighboring voxel respectively found, and
    steps for calculating the ratio r with the neighboring voxel found, the material assignment resulting therefrom being done to the assigned respective voxel from the assigning.

7. The method as claimed in claim 1, wherein, before the assigning, the ratio r is corrected using a correction term dependent on a diameter of the object to obtain the value r', the assigning being based on the value r'.

8. The method as claimed in claim 7, wherein the derived value r' is obtained by way of the following calculation rule, $r' = r + r_{corr}$, in which case $r_{corr} = a_{diam} * (d - 7.87)$, d corresponding to a mean diameter of the object in inches, and $a_{diam}$, to a coefficient.

9. A device for automatically differentiating at least one of bones and other calcium-containing materials and contrast agent in soft tissue of an object area, comprising:
a memory unit configured to store two image data records of the object area obtained from two computed tomography pictures of the object area at different spectral distributions of X-radiation, including X-ray attenuation values of voxels of the object area at the respective spectral distribution of the X-radiation, each voxel including two X-ray attenuation values corresponding to the two image data records; and
a determination module configured to calculate from the two image data records, for voxels of at least one slice of the object area, a ratio r, said ratio r resulting from at least one of the two X-ray attenuation values of the respective voxel and two averaged X-ray attenuation values that are obtained by averaging X-ray attenuation values of voxels inside a volume around the respective voxel in the respective image data record, and X-ray attenuation values o1, o2 of soft tissue or blood at the respective spectral distribution of the X-radiation, using the following equation, $$r = \frac{x_1 - o_1}{x_2 - o_2}$$

x1, x2 being the X-ray attenuation values or averaged X-ray attenuation values at the respective spectral distribution of the X-radiation, and to assign to the respective voxel upon overshooting of a threshold value for at least one of the ratio r and a value r' derived therefrom, either contrast agent or calcium-containing material as a function of a magnitude of at least one of r and r'.

10. The device as claimed in claim 9, wherein the determination module is further configured to, for each voxel, define a three-dimensional volume area around the voxel, to select inside the volume area all the voxels for which at least one of a mean value and a weighted mean value of the two X-ray attenuation values of the voxel is above a threshold value for contrast agent and calcium-containing materials or to select a number of voxels that have at least one of highest mean values and weighted mean values of the X-ray attenuation values inside the volume area, and to calculate an averaged X-ray attenuation value of the selected voxels separately for each image data record to determine the ratio r from the two averaged X-ray attenuation values.

11. The device as claimed in claim 9, wherein the determination module is further configured to, for each voxel, define a three-dimensional volume area around the voxel, to select inside the volume area all the voxels for which at least one of a mean value and a weighted mean value of the two X-ray attenuation values of the voxel is above a threshold value for contrast agent and calcium-containing materials or to select a number of voxels that have at least one of highest mean values and weighted mean values of the X-ray attenuation values inside the volume area, and to calculate an averaged X-ray attenuation value of the selected voxels separately for each image data record to determine the ratio r from the two averaged X-ray attenuation values, the determination of the ratio r of the averaged attenuation values being carried out only for voxels inside the volume area a number having at least one of a mean value and a weighted mean value of the two X-ray attenuation values above the threshold value for contrast agent and calcium-containing materials that lies above a minimum number.

12. The device as claimed in claim 10, wherein the weighted mean value $x_m$ is obtained from the following calculation rule, $$x_m = \frac{x_1 - m \cdot x_2}{1 - m}, \text{ in which case } m = -\frac{q^2}{r_{co,min}},$$

$x_1$ and $x_2$ representing the two X-ray attenuation values of the voxel at the two different spectral distributions of the X-radiation, $r_{co,min}$ representing a lower threshold value of the ratio r for contrast agent, and q representing a ratio of values of image noise of the images of the two image data records.

13. The device as claimed in claim 9, wherein the determination module is further configured to, before calculation of the ratio r, check whether a high proportion of voxels with a mean value of the X-ray attenuation values from the two image data records that is above a threshold value for contrast agent and calcium-containing materials occurs in a three-dimensional volume area around the voxel, and wherein, if a proportion is below a minimum value, the determination module is configured to search for a neighboring voxel from a group of neighboring voxels that has at least one of a highest mean value and weighted mean value of the X-ray attenuation values, and to repeat the search starting from the neighboring voxel respectively found and steps for calculating the ratio r with the neighboring voxel found, the material assignment resulting therefrom being done to the assigned respective voxel.

14. The device as claimed in claim 9, wherein the determination module is further configured to correct the ratio r before assigning either contrast agent or calcium-containing material to the respective voxel, using a correction term dependent on a diameter of the object to obtain the value r', derived from the ratio r, the assigning being based on the value r'.

15. The device as claimed in claim 14, wherein the determination module is further used to determine the derived value r' by way of the following calculation rule, $r' + r_{corr}$, in which case $r_{corr} = a_{diam} * (d - 7.87)$, d corresponding to a mean diameter of the object in inches, and $a_{diam}$ to a coefficient.

16. The method as claimed in claim 3, wherein the weighted mean value $x_m$ is obtained from the following calculation rule, $$x_m = \frac{x_1 - m \cdot x_2}{1 - m}, \text{ in which case } m = -\frac{q^2}{r_{co,min}},$$

$x_1$ and $x_2$ representing the two X-ray attenuation values of the voxel at the two different spectral distributions of the X-radiation, $r_{co,min}$ representing a lower threshold value of the ratio r for contrast agent, and q representing a ratio of values of image noise of the images of the two image data records.

17. The method as claimed in claimed in claim 16, wherein the ratio q of the image noise is determined in a preprocessing step from the two image data records or topograms recorded in advance.

18. The device as claimed in claim 11, wherein the weighted mean value $x_m$ is obtained from the following calculation rule, $$x_m = \frac{x_1 - m \cdot x_2}{1 - m}, \text{ in which case } m = -\frac{q^2}{r_{co,min}},$$

$x_1$ and $x_2$ representing the two X-ray attenuation values of the voxel at the two different spectral distributions of the X-radiation, $r_{co,min}$ representing a lower threshold value of the ratio r for contrast agent, and q representing a ratio of values of image noise of the images of the two image data records.

19. A device for automatically differentiating at least one of bones and other calcium-containing materials and contrast agent in soft tissue of an object area, comprising:
means for storing two image data records of the object area obtained from two computed tomography pictures of the object area at different spectral distributions of the X-radiation, including X-ray attenuation values of voxels of the object area at the respective spectral distribution of the X-radiation, each voxel including two X-ray attenuation values corresponding to the two image data records; and
means for calculating from the two image data records, for voxels of at least one slice of the object area, a ratio r-, said ratio r resulting from at least one of the two X-ray attenuation values of the respective voxel and two averaged X-ray attenuation values that are obtained by averaging X-ray attenuation values of voxels inside a volume around the respective voxel in the respective image data record, and X ray attenuation values o1, o2 of soft tissue or blood at the respective spectral distribution of the X-radiation, using the following equation, $$r = \frac{x_1 - o_1}{x_2 - o_2}$$

x1, x2 being the X-ray attenuation values or averaged X-ray attenuation values at the respective spectral distribution of the X-radiation, and the means for calculating being configured to assign to the respective voxel upon overshooting of a threshold value for at least one of the ratio r and a value r' derived therefrom, contrast agent or calcium-containing material as a function of a magnitude of at least one of r and r'.

20. The device as claimed in claim 19, wherein the means for calculating, for each voxel, is further configured to define a three-dimensional volume area around the voxel, to select inside the volume area all the voxels for which at least one of a mean value and a weighted mean value of the two X-ray attenuation values of the voxel lies above a threshold value for contrast agent and calcium-containing materials or to select a number of voxels that have at least one of highest mean values and weighted mean values of the X-ray attenuation values inside the volume area, and to calculate an averaged X-ray attenuation value of the selected voxels separately for each image data record to determine the ratio r from the two averaged X-ray attenuation values.

* * * * *